United States Patent
Lee

(10) Patent No.: US 11,412,961 B2
(45) Date of Patent: Aug. 16, 2022

(54) BLOOD GLUCOSE MEASUREMENT DEVICE AND METHOD TO AUTOMATICALLY DETERMINE BLOOD GLUCOSE UNIT

(71) Applicant: PHILOSYS CO., LTD., Jeollabuk-do (KR)

(72) Inventor: Young Wook Lee, Gyeonggi-do (KR)

(73) Assignee: PHILOSYS CO., LTD., Jeollabuk-do (KR)

( * ) Notice: Subject to any disclaimer, the term of this patent is extended or adjusted under 35 U.S.C. 154(b) by 569 days.

(21) Appl. No.: 16/503,978

(22) Filed: Jul. 5, 2019

(65) Prior Publication Data

US 2020/0008720 A1 Jan. 9, 2020

(30) Foreign Application Priority Data

Jul. 9, 2018 (KR) .......................... 10-2018-0079114

(51) Int. Cl.
| | | |
|---|---|---|
| *A61B 5/145* | (2006.01) | |
| *A61B 5/00* | (2006.01) | |
| *A61B 5/1455* | (2006.01) | |
| *G01N 27/327* | (2006.01) | |
| *G01N 33/66* | (2006.01) | |

(52) U.S. Cl.
CPC ........ *A61B 5/14532* (2013.01); *A61B 5/1455* (2013.01); *A61B 5/7435* (2013.01); *A61B 2562/0295* (2013.01); *G01N 27/3273* (2013.01); *G01N 33/66* (2013.01)

(58) Field of Classification Search
CPC ............. A61B 5/1455; A61B 5/14551; A61B 5/14532; A61B 5/7435; A61B 2562/08; A61B 2562/0295; G01N 27/3273; G01N 33/66

See application file for complete search history.

(56) References Cited

U.S. PATENT DOCUMENTS

| | | | | |
|---|---|---|---|---|
| 7,645,421 | B2 * | 1/2010 | Groll | .................... G01N 33/558 422/50 |
| 8,861,804 | B1 * | 10/2014 | Johnson | .................. G06F 16/23 382/218 |
| 2003/0212317 | A1 * | 11/2003 | Kovatchev | ............. G16H 50/50 128/920 |
| 2010/0000862 | A1 | 1/2010 | Rao | |
| 2011/0015511 | A1 | 1/2011 | Bousamra et al. | |
| 2014/0122150 | A1 * | 5/2014 | Davis | ............. G06Q 10/063118 705/7.17 |

(Continued)

FOREIGN PATENT DOCUMENTS

| | | |
|---|---|---|
| JP | 2009162676 A | 7/2009 |
| KR | 20130074313 A | 7/2013 |

OTHER PUBLICATIONS

Extended European Search Report relating to European Application No. 19184755.7, dated Nov. 7, 2019.

*Primary Examiner* — Chu Chuan Liu
(74) *Attorney, Agent, or Firm* — Meunier Carlin & Curfman LLC

(57) ABSTRACT

Provided is a blood glucose measurement device and method. The blood glucose measurement device may determine a blood glucose unit to be provided to a user based on a user input and a region in which the device is positioned, and provide blood glucose data to the user using the determined blood glucose unit through a display.

18 Claims, 9 Drawing Sheets

(56) References Cited

U.S. PATENT DOCUMENTS

2014/0262828 A1  9/2014 Iyengar et al.
2014/0316715 A1  10/2014 Choi et al.
2015/0224247 A1* 8/2015 McDorman ........... A61M 5/003
                                              206/569

* cited by examiner

FIG. 9
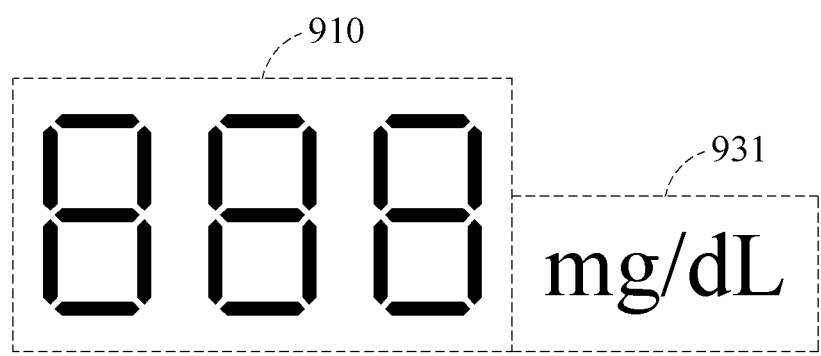
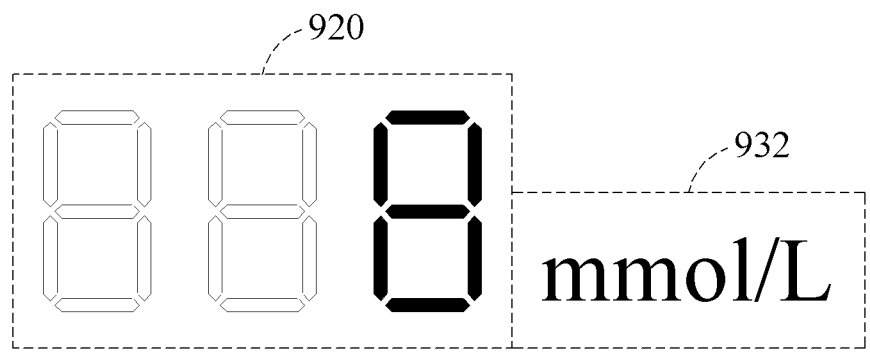

BLOOD GLUCOSE MEASUREMENT DEVICE AND METHOD TO AUTOMATICALLY DETERMINE BLOOD GLUCOSE UNIT

CROSS-REFERENCE TO RELATED APPLICATION(S)

This application claims the benefit of Korean Patent Application No. 10-2018-0079114, filed on Jul. 9, 2018, in the Korean Intellectual Property Office, the disclosure of which is incorporated herein by reference.

BACKGROUND

1. Field of the Invention

One or more example embodiments relate to blood glucose measurement technology for automatically changing a blood glucose unit.

2. Description of the Related Art

Recently, a growing number of modern people are suffering from so-called adult diseases such as diabetes, hyperlipemia, and thrombosis due to westernized dietary habits. Among young women, anemia patients with iron deficiency is increasing rapidly in number due to extreme diet. A simple method to know the severity of these adult diseases is measuring biocomponents in blood. The biocomponent measurement may detect quantities of a number of components in the blood, such as blood glucose, anemia, and blood coagulation, and thus an ordinary person may easily determine whether there is an abnormality, for example, whether a value of a specific component is in a normal region or an abnormal region, without seeing a doctor.

One easy biocomponent measurement is to quantitatively analyze an output signal using an electrochemical or photometric method after injecting a blood sample taken from a fingertip into a strip and inserting the strip into a biosensor. This biocomponent measurement is suitable for unprofessional ordinary people since a quantity of a corresponding component may be displayed on a measurement device.

Each country uses a different blood glucose unit to express a blood glucose level. Thus, there is a demand for technology for automatically providing a measured blood glucose level using a unit prescribed by the corresponding country without an additional control.

SUMMARY

An aspect provides a blood glucose measurement device that may determine a blood glucose unit based on geographical information.

An aspect provides a blood glucose measurement device that may determine a blood glucose unit based on an Internet address.

An aspect provides a blood glucose measurement device that may determine a blood glucose unit based on a code of a test strip.

An aspect provides a blood glucose measurement device that may determine a blood glucose unit based on a target blood glucose value input by a user.

According to an aspect, there is provided a blood glucose measurement method of automatically determining a blood glucose unit, the blood glucose measurement method including detecting a change in country information of a blood glucose measurement device by monitoring at least one of a user input and a region in which the blood glucose measurement device is positioned, determining a blood glucose unit corresponding to new country information, in response to an example in which a change in the country information is detected, and providing blood glucose data measured with respect to a user using the determined blood glucose unit.

The detecting may include changing the country information to a country indicated by the region in which the blood glucose measurement device is positioned, in response to an example in which the country indicated by the region changes.

The detecting may include calculating position estimation information with respect to the blood glucose measurement device, and determining a change in the country information based on a comparison between the position estimation information and a previous position of the blood glucose measurement device.

The calculating may include receiving a global navigation satellite system (GNSS) signal, and calculating position estimation information of the blood glucose measurement device based on the received GNSS signal.

The calculating may include identifying Internet Protocol (IP) address information assigned with respect to a computer network of the blood glucose measurement device, in response to an access to the computer network, and calculating the position estimation information based on the identified IP address information.

The detecting may include changing the country information of the blood glucose measurement device to a country corresponding to a new geographical position of the blood glucose measurement device, in response to an example in which the new geographical position is maintained longer than a threshold period.

The determining may include determining an expression unit corresponding to a country in which the blood glucose measurement device is positioned to be the blood glucose unit within a predetermined period close to a current point in time.

The detecting may include identifying a country code from a test strip, in response to an input of inserting the test strip, and detecting a change in the country information based on a comparison between the identified country code and current country information of the blood glucose measurement device.

The determining may include obtaining a target blood glucose value from the user input, and determining the blood glucose unit based on the obtained target blood glucose value.

The determining may include determining a first unit to be the blood glucose unit, in response to an example in which the obtained target blood glucose value is within a first range, and determining a second unit different from the first unit to be the blood glucose unit, in response to an example in which the obtained target blood glucose value is within a second range different from the first range.

The determining may include determining the blood glucose unit based on a number of digits of the obtained target blood glucose value.

The determining may include determining a first unit to be the blood glucose unit, in response to an example in which a number of digits of the obtained target blood glucose value exceeds a first threshold number of digits, and determining a second unit to be the blood glucose unit, in response to an example in which the number of digits of the obtained target blood glucose value is less than a second threshold number of digits.

The detecting may include identifying optical recognition information associated with a test strip, and detecting a change in the country information based on the optical recognition information.

The determining may include requesting expression unit definition information corresponding to the new country information from a server, and determining the blood glucose unit to be an expression unit of blood glucose defined by the expression unit definition information, in response to an example in which the expression unit definition information limits the expression unit.

The detecting may include detecting a change in the country information based on at least one of a network service provider to which the blood glucose measurement device is connected, a subscriber identity module (SIM) card, and a user setting language.

The determining may include selecting one unit from a plurality of blood glucose units based on the user input, in response to an example in which a new country supports the plurality of blood glucose units, and determining the selected unit to be the blood glucose unit.

The blood glucose measurement method may further include initializing the blood glucose unit when the blood glucose measurement device senses blood glucose data for the first time.

The providing may include sensing blood glucose data measured with respect to the user, from a test strip inserted into a blood glucose measurement module connected to the blood glucose measurement device, and visualizing the sensed blood glucose data using the determined blood glucose unit.

According to an aspect, there is provided a blood glucose measurement device for automatically determining a blood glucose unit, the blood glucose measurement device including a processor configured to detect a change in country information of a blood glucose measurement device by monitoring at least one of a user input and a region in which the blood glucose measurement device is positioned, and determine a blood glucose unit corresponding to new country information, in response to an example in which a change in the country information is detected, and an outputter configured to provide blood glucose data measured with respect to a user using the determined blood glucose unit.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIGS. 8 and 9 illustrate an example of determining a blood glucose unit based on a number of digits of a target blood glucose value according to an example embodiment.

DETAILED DESCRIPTION

Figure 1:
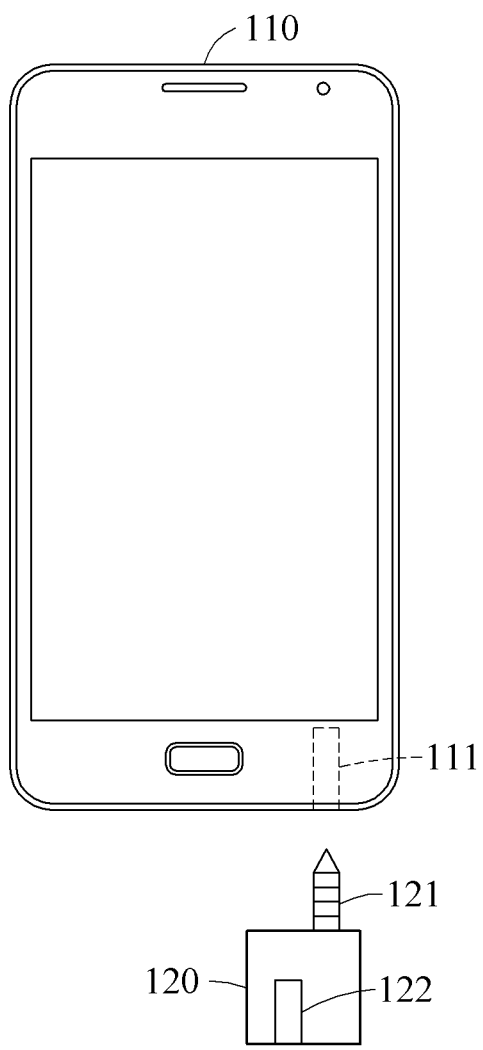
FIG. 1 illustrates a configuration of a blood glucose measurement system according to an example embodiment.

Hereinafter, some example embodiments will be described in detail with reference to the accompanying drawings. However, various alterations and modifications may be made to the example embodiments. Here, the example embodiments are not construed as limited to the disclosure and should be understood to include all changes, equivalents, and replacements within the idea and the technical scope of the disclosure.

The terminology used herein is for the purpose of describing particular examples only and is not to be limiting of the examples. As used herein, the singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which examples belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the examples with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

FIG. 1 illustrates a configuration of a blood glucose measurement system according to an example embodiment.

A blood glucose measurement system 100 may include a blood glucose measurement device 110 and a blood glucose measurement module 120.

The blood glucose measurement device 110 may be a device that may be connected to the blood glucose measurement module 120. The blood glucose measurement device 110 may include a socket 111 to be connected to a plug 121 of the blood glucose measurement module 120. The blood glucose measurement device 110 may be implemented as a smart device, such as for example, a smart phone. The blood glucose measurement device 110 may include a display to display a blood glucose measurement result, and a power supply to supply power. For example, the socket 111 of the blood glucose measurement device 110 may be a microphone socket.

The blood glucose measurement device 110 may receive, from the blood glucose measurement module 120, sequence data indicating a blood glucose level measured by the blood glucose measurement module 120. The sequence data may be information indicating a blood glucose level, and include a series of data signals. The sequence data may also be referred to as blood glucose data. The blood glucose measurement device 110 may sequentially receive the series of data signals. The blood glucose measurement device 110 may determine bits indicated by the respective data signals by reading the data signals. The bits indicated by the respective data signals may be, for example, values of "0" or "1".

The blood glucose measurement device 110 may store an application program for blood glucose measurement to process and manage sequence data indicating a blood glucose level.

When the socket 111 of the blood glucose measurement device 110 is connected to the plug 121 of the blood glucose measurement module 120 for use, the blood glucose measurement module 120 may use all an input, an output, and a power of the blood glucose measurement device 110. Further, a data communication scheme between the blood glucose measurement device 110 and the blood glucose measurement module 120 may be a frequency shift keying (FSK) scheme. However, example embodiments are not limited thereto. The data communication scheme may be designed differently depending on a purpose of use and a means.

For example, the blood glucose measurement device 110 may include a phone jack socket 111 to be connected to a phone jacket plug 121 of the blood glucose measurement module 120 or a port to be connected to a pin plug 121. However, the type and the shape of the socket 111 of the blood glucose measurement device 110 are not limited thereto. In a connection structure using the pin, the blood glucose measurement device 110 may include the plug 121, and the blood glucose measurement module 120 may include the socket 111.

The blood glucose measurement module 120 may measure a blood glucose level in the blood absorbed by a test strip, and transmit a data signal indicating the measured blood glucose level to the blood glucose measurement device 110 in response to a connection to the blood glucose measurement device 110. The blood glucose measurement module 120 may be connected to the socket 111 of the blood glucose measurement device 110 for use. For example, when the plug 121 of the blood glucose measurement module 120 is connected to the socket 111 of the blood glucose measurement device 110, a connection between the blood glucose measurement module 120 and the blood glucose measurement device 110 may be built. The blood glucose measurement module 120 may measure and calculate the blood glucose level in the blood absorbed by the test strip using the power supplied from the power supply of the blood glucose measurement device 110, in response to an example in which a connection to the blood glucose measurement device 110 is detected. The blood glucose measurement module 120 may transmit sequence data including information indicating the blood glucose level to the blood glucose measurement device 110.

The blood glucose measurement module 120 may include a main body, a strip insertion hole 122, and the plug 121.

The main body of the blood glucose measurement module 120 may include a blood glucose measuring unit for measuring the blood glucose level in the blood absorbed by the test strip, and a central processing unit for calculating and transmitting a blood glucose level measurement result. The main body of the blood glucose measurement module 120 does not need to include a power supply and a display and thus, the size and the weight thereof may be reduced.

The strip insertion hole 122 may be formed in a portion of the main body, and have a structure into which the test strip may be inserted. The strip insertion hole 122 may be implemented in a structure into which the test strip may be inserted. However, the structure and the design are not limited thereto.

The plug 121 may be formed on one end surface of the main body and have a structure that may be connected to the socket 111 of the blood glucose measurement device 110. As described above, the plug 121 may be a phone jack plug or a pin plug. However, example embodiments are not limited thereto.

The test strip may be a strip formed of a material that may absorb blood.

For reference, when the blood glucose measurement device 110 is implemented as a smart phone, the blood glucose measurement device 110 may execute an application for blood glucose measurement. After the application for blood glucose measurement is executed, the blood glucose measurement device 110 may determine whether the plug 121 of the blood glucose measurement module 120 is connected to the socket 111. When a connection between the blood glucose measurement module 120 and the blood glucose measurement device 110 is built, the blood glucose measurement module 120 may receive power supplied from the power source of the blood glucose measurement device 110, and the blood glucose measurement module 120 may perform an internal test. When there is no abnormality in the internal test, the blood glucose measurement device 110 may display a screen for requesting strip insertion through the display. In response to an example in which a user inserts the test strip into the strip insertion hole 122 of the blood glucose measurement module 120, the blood glucose measurement device 110 may display a strip expiration check screen, and check whether the test strip expires. When the test strip is determined to be normal, the blood glucose measurement device 110 may display a blood injection screen through the display.

In response to an example in which the blood of the user is injected into the test strip, the blood glucose measurement module 120 may transmit data indicating a blood glucose level to the blood glucose measurement device 110. The blood glucose measurement device 110 may display a screen showing that the blood glucose measurement is in progress, and calculate a blood glucose measurement result from the data received from the blood glucose measurement module 120. The blood glucose measurement device 110 may display the blood glucose measurement result, and further store the blood glucose measurement result.

Figure 2:
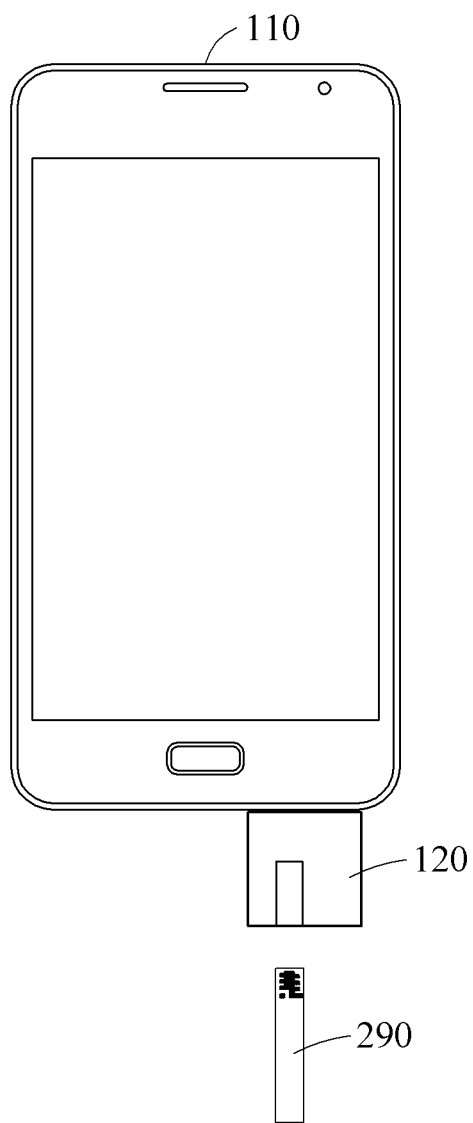
FIG. 2 illustrates a test strip to be inserted into a blood glucose measurement system according to an example embodiment.

FIG. 2 illustrates a test strip to be inserted into a blood glucose measurement system according to an example embodiment.

The blood glucose measurement device 110 and the blood glucose measurement module 120 of FIG. 1 may be connected as shown in FIG. 2. When a test strip 290 is inserted into the blood glucose measurement module 120, the blood glucose measurement device 110 may receive blood glucose data sensed from the test strip 290 by the blood glucose measurement module 120, and provide the blood glucose data to a user.

The test strip 290 may be a strip which converts an analyte into a predetermined signal. Herein, the analyte may be a material associated with a living body. The analyte may be a substance which is a subject of analysis. For example, the analyte may be a blood glucose. However, example embodiments are not limited thereto. For example, the test strip 290 may be a type of transducer which converts an amount of an analyte into an electrical signal in response to a reaction with the analyte. The test strip 290 may include, for example, a blood glucose strip. The blood glucose strip may be a test strip chemically manufactured to be stained with blood, and include an enzyme which has a chemical reaction by reacting with a blood glucose in the blood. Hereinafter, an example in which the test strip 290 is a blood glucose strip will be principally described. However, example embodiments are not limited thereto.

In an example, an electrode portion may be formed on one surface of the test strip 290. The electrode portion may include a reaction portion and a code indication portion. A form of the electrode portion formed on the test strip 290, for example, a form of the code indication portion, may indicate a predetermined code sequence. For example, the test strip 290 may be inserted into a strip insertion hole of the blood glucose measurement device 110 in an insertion direction, and the blood glucose measurement device 110 may automatically recognize the code sequence from the form of the code indication portion. The strip insertion hole may include at least one pin to form a connection with the code indication portion of the test strip 290.

Herein, the code sequence may be a sequence including a series of codes. A code may be a bit value of "0" or a bit value of "1". For example, when the code sequence includes n codes, the code sequence may be n bits. If n is "3" and the n codes are respectively "1", "1", and "0", the code sequence may indicate a binary value "110". The binary value "110" corresponds to a decimal number of $2^2+2^1+2^0$="6". n may be an integer greater than or equal to "1". The code sequence may indicate, for example, a country code of a country where the test strip is sold.

Figure 3:
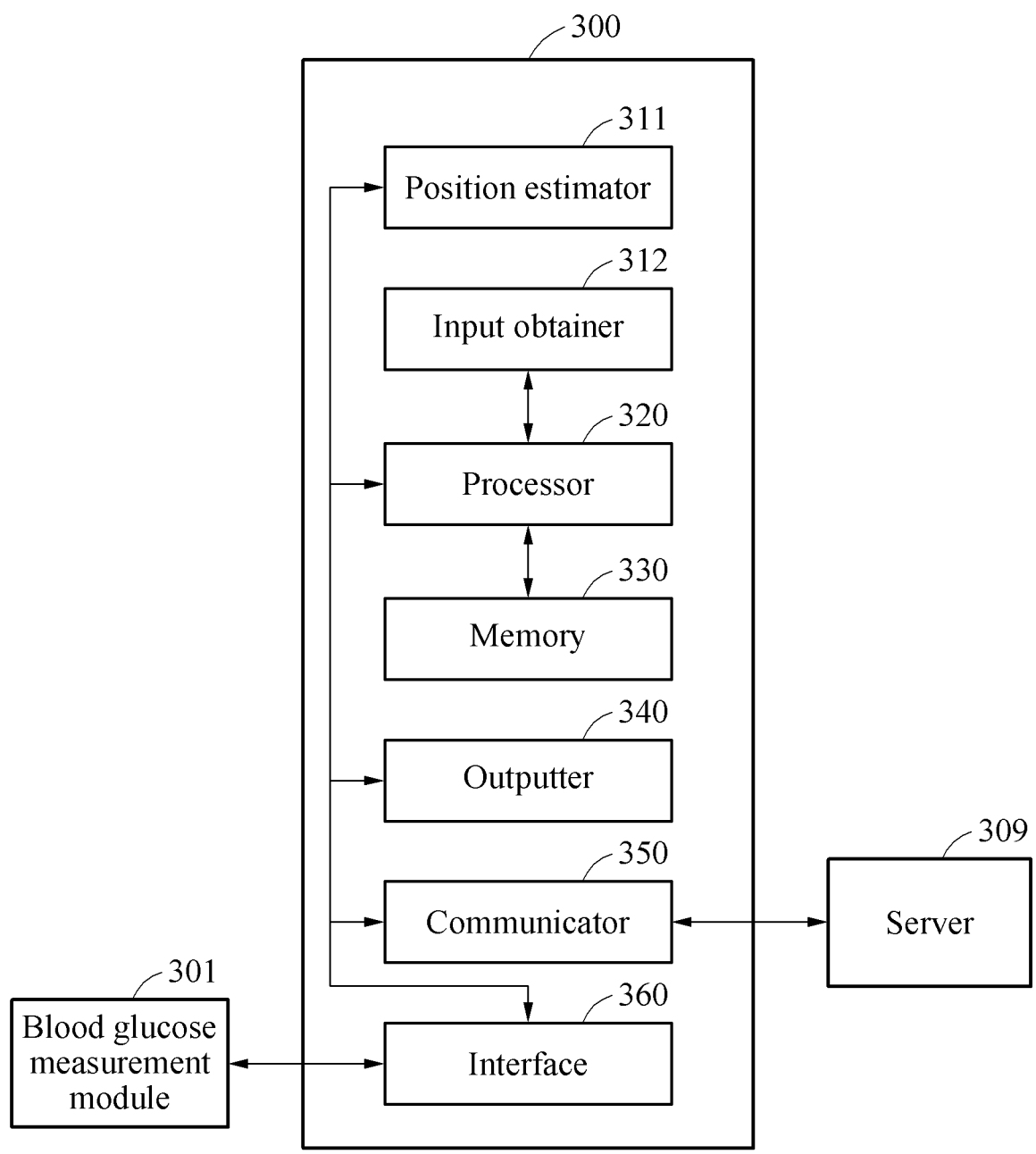
FIG. 3 is a block diagram illustrating a configuration of a blood glucose measurement device according to an example embodiment.

FIG. 3 is a block diagram illustrating a configuration of a blood glucose measurement device according to an example embodiment.

A blood glucose measurement device 300 may sense blood glucose data measured and transmitted by a blood glucose measurement module 301. Further, the blood glucose measurement device 300 may receive expression unit definition information from a server 309. The expression unit definition information may be information which defines a blood glucose unit which needs to be used in a predetermined country.

The blood glucose measurement module 301 may measure a blood glucose level in the blood absorbed by a test strip, and transmit a data signal, for example, blood glucose data, indicating the measured blood glucose level to the blood glucose measurement device 300 in response to a connection to the blood glucose measurement device 300, as described with reference to FIG. 1.

The server 309 may be an external server of the blood glucose measurement device 300, and store expression unit definition information. However, the server 309 is not limited thereto. The server 309 may store information required to determine a blood glucose unit, and transmit information requested by the blood glucose measurement device 300 to the blood glucose measurement device 300.

The blood glucose measurement device 300 may include a position estimator 311, an input obtainer 312, a processor 320, a memory 330, an outputter 340, a communicator 350, and an interface 360.

The position estimator 311 may estimate a position of the blood glucose measurement device 300. For example, the position estimator 311 may receive a global navigation satellite system (GNSS) signal. The position estimator 311 may calculate position estimation information of the blood glucose measurement device 300 based on the received GNSS signal. The position estimation information may be information estimated with respect to a geographical position of the blood glucose measurement device 300.

The input obtainer 312 may obtain a user input from a user. The user input may be, for example, a motion of inputting a target blood glucose value. The target blood glucose value may be a blood glucose level desired by the user to maintain. In an example, the input received through the input obtainer 312 may be converted into an instruction associated with blood glucose data provision by the processor 320. For example, the instruction associated with blood glucose data provision may include an instruction for indicating a blood glucose unit, an instruction for inputting a target blood glucose value, and an instruction for selecting one unit from a plurality of blood glucose units. Hereinafter, the input may include inputs by all manipulations received from the user while the blood glucose data is provided.

The processor 320 may detect a change in country information of the blood glucose measurement device 300 by monitoring at least one of a user input and a region in which the blood glucose measurement device 300 is positioned. Further, the processor 320 may determine a blood glucose unit corresponding to new country information, in response to an example in which a change in the country information is detected. In addition, the processor 320 may perform processing required for an operation of the blood glucose measurement device 300. Here, to perform processing may be to execute program codes stored in the memory 330.

Herein, the country information may be information indicating a country in which the blood glucose measurement device is used.

The memory 330 may store a program including instructions for operating the blood glucose measurement device 300. The program stored in the memory 330 may be executed by the processor 320 described above. For example, the memory 330 may store a blood glucose measurement application. Furthermore, the memory 330 may store information related to blood glucose data provision.

The outputter 340 may provide the blood glucose data measured with respect to the user using the determined blood glucose unit. For example, the outputter 340 may display a screen associated with blood glucose measurement for the user. For example, the outputter 340 may visually represent the blood glucose data with the determined blood glucose unit.

The communicator 350 may communicate with the server 309. For example, the communicator 350 may communicate with the server 309 using at least one of wireless communication and wired communication. In an example, the communicator 350 may transmit a request for expression unit information to the server 309.

The interface 360 may build data communication with an external device or module. For example, the interface 360 may be connected to the blood glucose measurement module 301, and receive the blood glucose data from the blood glucose measurement module 301. Further, the interface 360 may load data stored in an external memory card from the corresponding memory card.

In an example, the processor 320 may request expression unit definition information corresponding to new country information from the server 309 through the communicator 350. The processor 320 may determine the blood glucose unit to be an expression unit of blood glucose defined by the expression unit definition information, in response to an example in which the expression unit definition information limits the expression unit.

Further, a predetermined country may allow at least two expression units. The processor 320 of the blood glucose measurement device 300 may select one of a plurality of blood glucose units based on a user input, in response to an example in which a country in which the blood glucose measurement device 300 is positioned supports the plurality of blood glucose units. The processor 320 may determine the selected unit to be the blood glucose unit.

Figure 4:
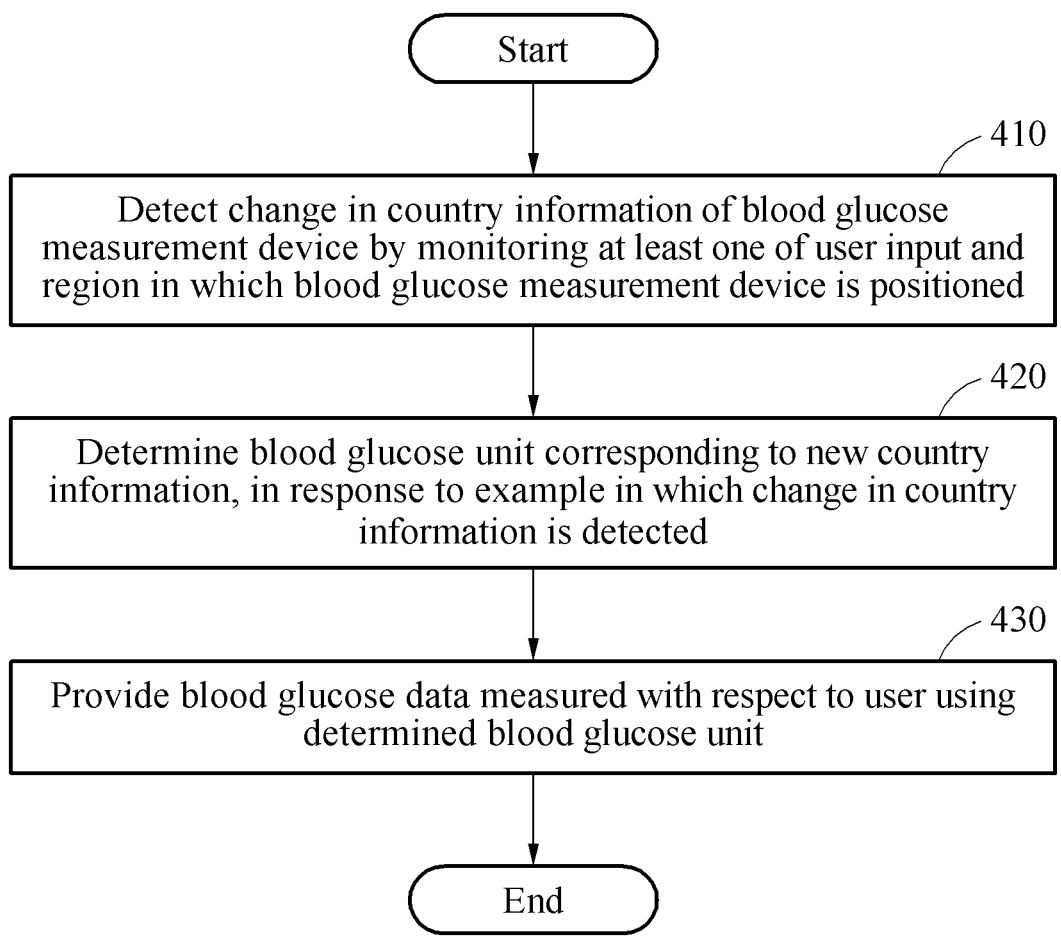
FIG. 4 is a flowchart illustrating a blood glucose measurement method according to an example embodiment.

FIG. 4 is a flowchart illustrating a blood glucose measurement method according to an example embodiment.

In operation 410, a blood glucose measurement device may detect a change in country information of the blood glucose measurement device by monitoring at least one of a user input and a region in which the blood glucose measurement device is positioned. The blood glucose measurement device may change the country information to a country indicated by the region in which the blood glucose measurement device is positioned, in response to an example in which the country indicated by the region changes. For example, the blood glucose measurement device may estimate the region in which the blood glucose measurement device is positioned based on Internet Protocol (IP) address information and position estimation information using a GNSS. In another example, the blood glucose measurement device may directly receive the region in which the blood glucose measurement device is positioned based on a user input, which will be described further with reference to FIGS. 5 through 7.

In operation 420, the blood glucose measurement device may determine a blood glucose unit corresponding to new country information, in response to an example in which a change in the country information is detected. The blood glucose measurement device may store a blood glucose unit corresponding to an individual country in a memory, and load a blood glucose unit corresponding to a new country from the memory. For example, the blood glucose measurement device may store, in the memory, a list in which a blood glucose unit required to be used in an individual country is mapped to the corresponding country. An example of determining a blood glucose unit based on a number of digits of a target blood glucose value will be described below with reference to FIGS. 8 and 9.

In operation 430, the blood glucose measurement device may provide blood glucose data measured with respect to a user using the determined blood glucose unit. The blood glucose measurement device may sense the blood glucose data measured with respect to the user, from a test strip inserted into a blood glucose measurement module connected to the blood glucose measurement device. The blood glucose measurement device may visualize the sensed blood glucose data using the determined blood glucose unit.

The blood glucose measurement device may initialize the blood glucose unit when the blood glucose measurement device senses blood glucose data for the first time. For example, the blood glucose measurement device may initialize the blood glucose unit to a unit automatically estimated based on position information or a unit manually input by the user at a time of first operation. In another example, the blood glucose measurement device may determine the blood glucose unit to be a default unit stored in the device.

Figure 5:
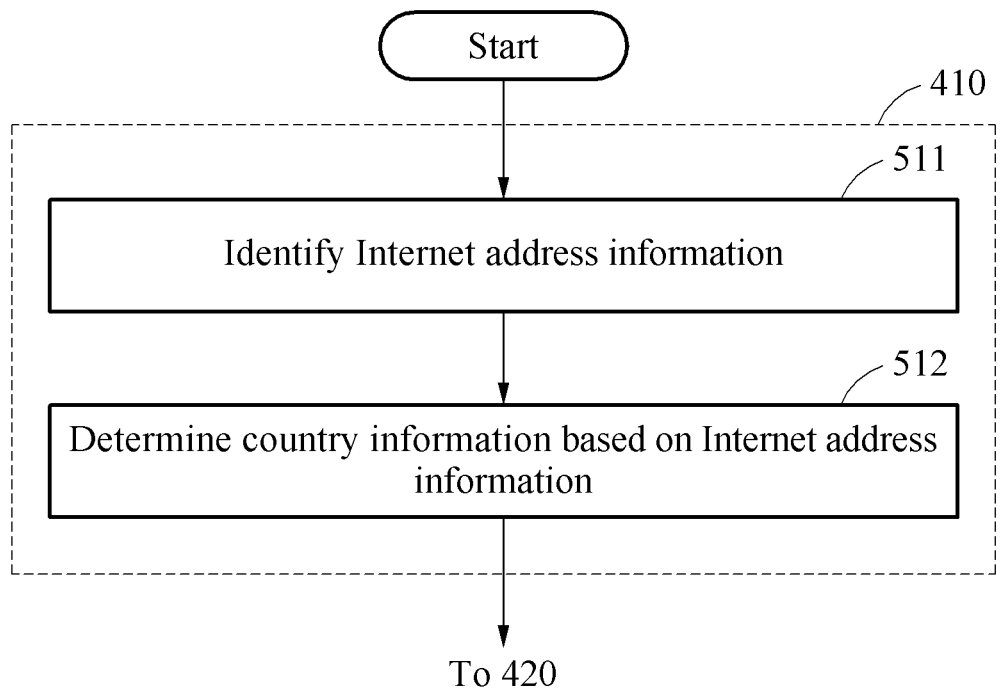
FIGS. 5 through 7 are flowcharts illustrating examples of detecting a change in country information according to an example embodiment.
Figure 6:
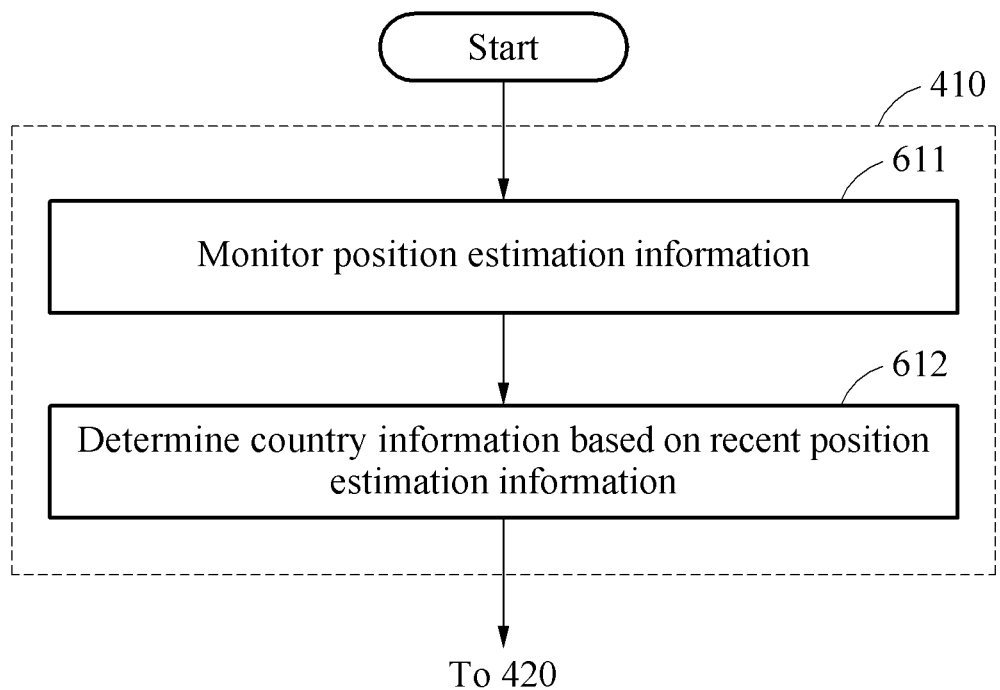
Figure 7:
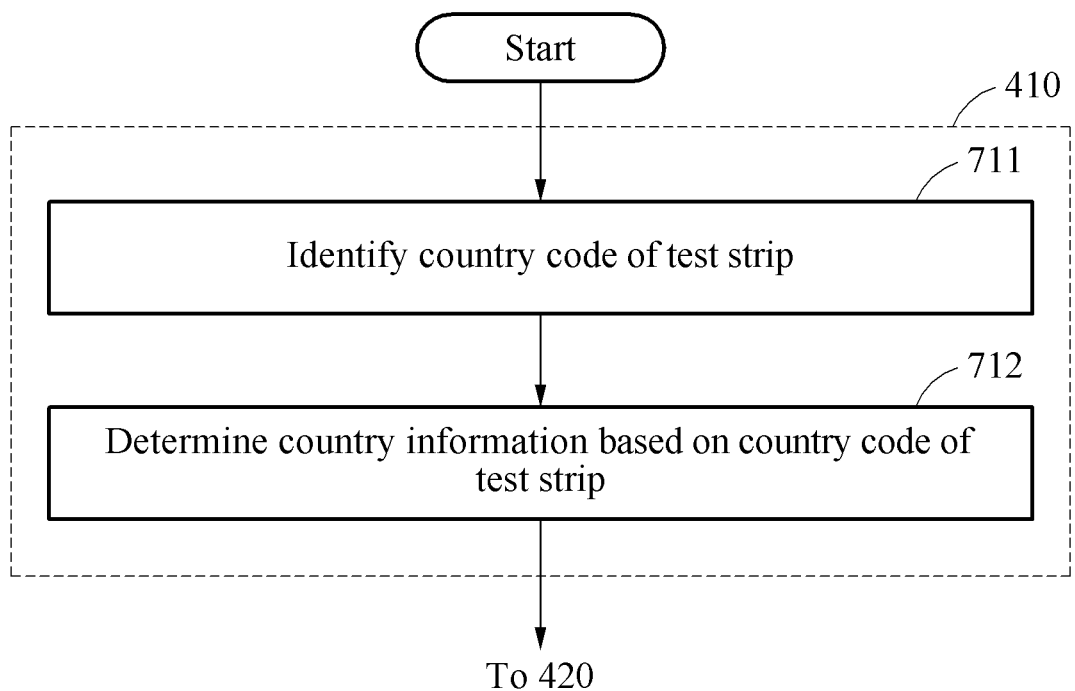

FIGS. 5 through 7 are flowcharts illustrating examples of detecting a change in country information according to an example embodiment.

Referring to FIG. 5, in operation 511, the blood glucose measurement device may identify Internet address information. For example, the blood glucose measurement device may identify IP address information assigned with respect to a computer network of the blood glucose measurement device, in response to an access to the computer network.

In operation 512, the blood glucose measurement device may determine the country information based on the Internet address information. For example, the blood glucose measurement device may estimate the region in which the blood glucose measurement device is positioned based on the Internet address information, and determine a country to which the estimated region belongs to be the country information.

Referring to FIG. 6, in operation 611, the blood glucose measurement device may monitor position estimation information. The blood glucose measurement device may calculate the position estimation information with respect to the blood glucose measurement device. For example, the blood glucose measurement device may receive a GNSS signal. The blood glucose measurement device may calculate the position estimation information of the blood glucose measurement device based on the received GNSS signal. In another example, the blood glucose measurement device may calculate the position estimation information based on a time line.

In operation 612, the blood glucose measurement device may determine the country information based on recent position estimation information. The blood glucose measurement device may determine a change in the country information based on a comparison between the position estimation information and a previous position of the blood glucose measurement device. The blood glucose measurement device may determine that the country information changes, in response to an example in which the position estimation information differs from the previous position.

The blood glucose measurement device may change the country information of the blood glucose measurement device to a country corresponding to a new geographical position of the blood glucose measurement device, in response to an example in which the new geographical position is maintained longer than a threshold period. The threshold period may vary depending on a design. The threshold period may be set in days. If the new geographical position is maintained longer than the threshold period, for example, 7 days, the blood glucose measurement device may determine that the user resides in the corresponding region. The blood glucose measurement device may request whether to approve a change of the blood glucose unit from the user, in response to an example in which a length of stay of the user exceeds the threshold period. The blood glucose measurement device may maintain the threshold period if the change of the blood glucose unit is approved, and may increase the threshold period if the change of the blood glucose unit is rejected. However, an adjustment of the threshold period is not limited thereto, and the threshold period may vary depending on a design.

The blood glucose measurement device may determine an expression unit corresponding to a country in which the blood glucose measurement device is positioned to be the blood glucose unit within a predetermined period close to a current point in time. Thus, the blood glucose measurement device may specify a country in which the user is positioned based on a last region in which the user was positioned.

Referring to FIG. 7, in operation 711, the blood glucose measurement device may identify a country code of a test strip. The blood glucose measurement device may identify the country code from the test strip, for example, in response to an input of inserting the test strip. The blood glucose measurement device may automatically identify a form of the code indication portion when the test strip is inserted into the blood glucose measurement module, and read a series of code sequences from the identified form. The blood glucose measurement device may determine a country code corresponding to the read code sequences.

In operation 712, the blood glucose measurement device may determine the country information based on the country code of the test strip. For example, the blood glucose measurement device may detect a change in the country information based on a comparison between the identified country code and current country information of the blood glucose measurement device. The blood glucose measurement device may determine that the country information changes, in response to an example in which a country indicated by the country code identified from the test strip differs from the current country information. The blood glucose measurement device may change the country information to the country corresponding to the country code identified from the test strip.

However, an operation of detecting a change in the country information is not limited to the examples of FIGS. 5 through 7. For example, the blood glucose measurement device may also detect a change in the country information based on at least one of a network service provider to which the blood glucose measurement device is connected, a subscriber identity module (SIM) card, and a user setting language. The network service provider may be a business that provides a communication network, and each country has different businesses. Thus, the blood glucose measurement device may identify a country based on the network service provider. A SIM card is provided by a network service provider of an individual country, and thus the blood glucose measurement device may also identify a country based on the SIM card. In addition, the blood glucose measurement device may identify a country based on a user setting language set by the user.

In still another example, the blood glucose measurement device may identify optical recognition information associated with the test strip. The blood glucose measurement device may identify a country code printed in a form of a quick response (QR) code or barcode on a packaging material of the test strip. The optical recognition information may include the country code provided in the form of the QR code or barcode. The blood glucose measurement device may detect a change in the country information based on the optical recognition information. For example, when the blood glucose measurement device optically recognizes the country code based on a user input, the blood glucose measurement device may determine a country corresponding to the recognized country code.

Figure 8:
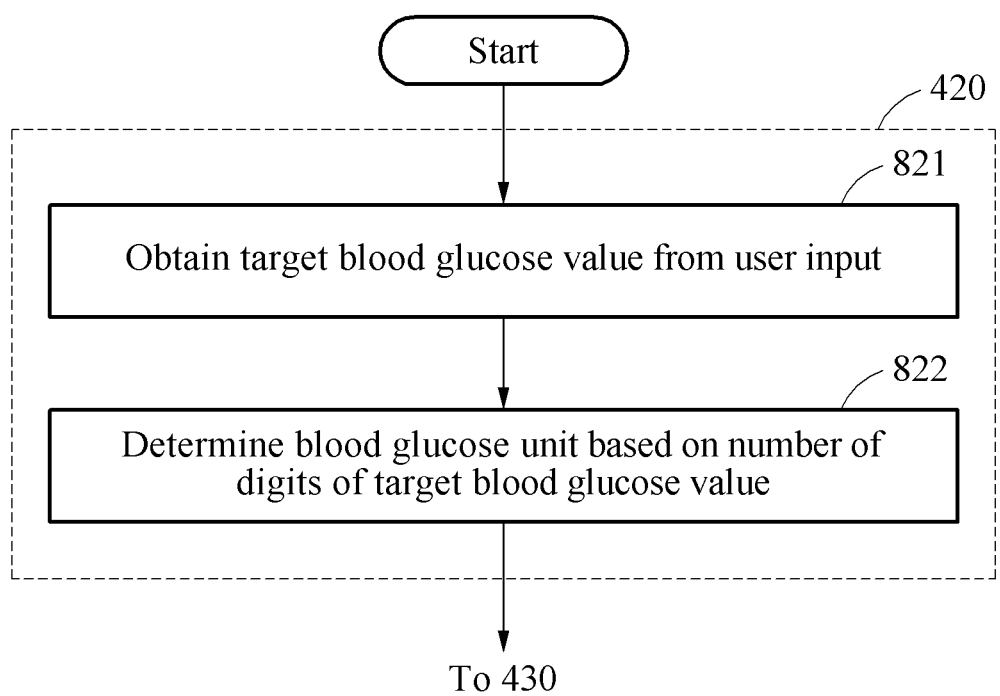

FIGS. 8 and 9 illustrate an example of determining a blood glucose unit based on a number of digits of a target blood glucose value according to an example embodiment.

In operation 821, a blood glucose measurement device may obtain a target blood glucose value from a user input.

In operation 822, the blood glucose measurement device may determine a blood glucose unit based on the obtained target blood glucose value. For example, the blood glucose measurement device may determine a first unit to be the blood glucose unit, in response to an example in which the obtained target blood glucose value is within a first range. The blood glucose measurement device may determine a second unit different from the first unit to be the blood glucose unit, in response to an example in which the obtained target blood glucose value is within a second range different from the first range. For example, the first range may be a range exceeding a threshold value, and the second range may be a range below the threshold value. The first unit may be, for example, milligrams per deciliter (mg/dL), and the second unit may be, for example, millimoles per liter (mmol/L). The blood glucose measurement device may determine that a user intends to use a unit of mg/dL, in response to an example in which the target blood glucose value exceeds the threshold value. The blood glucose measurement device may determine that the user intends to use a unit of mmol/L, in response to an example in which the target blood glucose value is less than or equal to the threshold value.

Further, the blood glucose measurement device may determine the blood glucose unit based on a number of digits of the obtained target blood glucose value. The number of digits may be, for example, a number of significant digits, and be a number of figures at integer parts in the units place or higher places of a decimal number. For example, the blood glucose measurement device may determine the first unit to be the blood glucose unit, in response to an example in which the number of digits of the obtained target blood glucose value exceeds a first threshold number of digits.

The blood glucose measurement device may determine the second unit to be the blood glucose unit, in response to an example in which the number of digits of the obtained target blood glucose value is less than a second threshold number of digits. The first threshold number of digits and the second threshold number of digits may be "2". For example, referring to FIG. 9, with respect to a first target blood glucose level 910 of 3 digits, the blood glucose measurement device may determine a first unit 931, for example, mg/dL, to be the blood glucose unit. With respect to a second target blood glucose level 920 of 1 digit, the blood glucose measurement device may determine a second unit 932, for example, mmol/L, to be the blood glucose unit. A human blood glucose level may not be expressed in 3 digits if a unit of mmol/L is used, and thus the blood glucose measurement device may express a 3-digit target blood glucose value with mg/dL. Conversely, a human blood glucose level may not be expressed in 1 digit if a unit of mg/dL is used, and thus the blood glucose measurement device may express a 1-digit target blood glucose value with mmol/L.

The first threshold number of digits and the second threshold number of digits described above are provided for ease of description, and thus example embodiments are not limited thereto.

In the blood glucose measurement device, an order of the operations described with reference to FIGS. 1 through 9 is not limited to the description provided above, and may vary depending on a design. Further, each operation described with reference to FIGS. 1 through 9 may be performed by being combined with the other operations, and some of the operations may be omitted. Further, the blood glucose measurement device may determine a plurality of blood glucose units through the operations described with reference to FIGS. 4 through 8, or may determine an expression unit with highest reliability among the plurality of blood glucose units.

According to example embodiments, a blood glucose measurement device may detect whether a county in which the blood glucose measurement device is used changes based on geographical information, and visualize blood glucose data using an expression unit corresponding to the country.

According to example embodiments, a blood glucose measurement device may detect whether a country in which the blood glucose measurement device is used changes based on an Internet address, and visualize blood glucose data using an expression unit corresponding to the country.

According to example embodiments, a blood glucose measurement device may identify a country in which the blood glucose measurement device is used, by identifying a country code implemented in a form of an electrode on a test strip.

According to example embodiments, a blood glucose measurement device may determine an expression unit of blood glucose based on a number of digits of a target blood glucose value desired by a user to maintain.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

The software may include a computer program, a piece of code, an instruction, or some combination thereof, to independently or collectively instruct or configure the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A blood glucose measurement method of automatically determining a blood glucose unit, the blood glucose measurement method comprising:
   detecting a change in country information of a blood glucose measurement device by monitoring at least one of a user input and a region in which the blood glucose measurement device is positioned;
   in response to detecting the change in the country information, determining a blood glucose unit corresponding to new country information; and
   providing blood glucose data measured with respect to a user using the determined blood glucose unit,
   wherein the determining comprises:
   obtaining a target blood glucose value which is a blood glucose level desired by a user to maintain from the user input;
   in response to the obtained target blood glucose value being within a first range, determining a first unit to be the blood glucose unit; and
   in response to the obtained target blood glucose value being within a second range different from the first range, determining a second unit different from the first unit to be the blood glucose unit.

2. The blood glucose measurement method of claim 1, wherein the detecting comprises changing the country information to a country indicated by the region in which the blood glucose measurement device is positioned, in response to a change in the country indicated by the region.

3. The blood glucose measurement method of claim 1, wherein the detecting comprises:
   calculating position estimation information with respect to the blood glucose measurement device; and
   determining a change in the country information based on a comparison between the position estimation information and a previous position of the blood glucose measurement device.

4. The blood glucose measurement method of claim 3, wherein the calculating comprises:
   receiving a global navigation satellite system (GNSS) signal; and
   calculating position estimation information of the blood glucose measurement device based on the received GNSS signal.

5. The blood glucose measurement method of claim 3, wherein the calculating comprises:
   identifying Internet Protocol (IP) address information assigned with respect to a computer network of the blood glucose measurement device, in response to an access to the computer network; and
   calculating the position estimation information based on the identified IP address information.

6. The blood glucose measurement method of claim 1, wherein the detecting comprises changing the country information of the blood glucose measurement device to a country corresponding to a new geographical position of the blood glucose measurement device, in response to the new geographical position being maintained longer than a threshold period.

7. The blood glucose measurement method of claim 1, wherein the determining comprises determining an expression unit corresponding to a country in which the blood glucose measurement device is positioned to be the blood glucose unit within a predetermined period close to a current point in time.

8. The blood glucose measurement method of claim 1, wherein the detecting comprises:
   identifying a country code from a test strip, in response to an input of inserting the test strip; and
   detecting a change in the country information based on a comparison between the identified country code and current country information of the blood glucose measurement device.

9. The blood glucose measurement method of claim 1, wherein the determining comprises determining the blood glucose unit based on a number of digits of the obtained target blood glucose value.

10. The blood glucose measurement method of claim 1, wherein the determining comprises:
   determining a first unit to be the blood glucose unit, in response to a number of digits of the obtained target blood glucose value exceeding a first threshold number of digits; and
   determining a second unit to be the blood glucose unit, in response to the number of digits of the obtained target blood glucose value being less than a second threshold number of digits.

11. The blood glucose measurement method of claim 1, wherein the detecting comprises:
   identifying optical recognition information associated with a test strip; and
   detecting a change in the country information based on the optical recognition information.

12. The blood glucose measurement method of claim 1, wherein the determining comprises:
   requesting expression unit definition information corresponding to the new country information from a server; and
   determining the blood glucose unit to be an expression unit of blood glucose defined by the expression unit definition information, in response to the expression unit definition information limiting the expression unit.

13. The blood glucose measurement method of claim 1, wherein the detecting comprises detecting a change in the country information based on at least one of a network service provider to which the blood glucose measurement device is connected, a subscriber identity module (SIM) card, and a user setting language.

14. The blood glucose measurement method of claim 1, wherein the determining comprises:
   selecting one unit from a plurality of blood glucose units based on the user input, in response to a new country supporting the plurality of blood glucose units; and
   determining the selected unit to be the blood glucose unit.

15. The blood glucose measurement method of claim 1, further comprising:
   initializing the blood glucose unit when the blood glucose measurement device senses blood glucose data for the first time.

16. The blood glucose measurement method of claim 1, wherein the providing comprises:
   sensing blood glucose data measured with respect to the user, from a test strip inserted into a blood glucose measurement module connected to the blood glucose measurement device; and
   visualizing the sensed blood glucose data using the determined blood glucose unit.

17. A non-transitory computer-readable storage medium storing instructions that, when executed by a processor, cause the processor to perform the blood glucose measurement method of claim 1.

18. A blood glucose measurement device for automatically determining a blood glucose unit, the blood glucose measurement device comprising:
   a processor configured to detect a change in country information of a blood glucose measurement device by monitoring at least one of a user input and a region in which the blood glucose measurement device is positioned, and determine a blood glucose unit corresponding to new country information, in response to detecting a change in the country information; and
   an outputter configured to provide blood glucose data measured with respect to a user using the determined blood glucose unit,
   wherein the processor configured to obtain a target blood glucose value which is a blood glucose level desired by a user to maintain from the user input, determine a first unit to be the blood glucose unit, in response to the obtained target blood glucose value being within a first range, and determine a second unit different from the first unit to be the blood glucose unit, in response to the obtained target blood glucose value being within a second range different from the first range.

* * * * *